United States Patent [19]

Shelton

[11] 4,120,948
[45] Oct. 17, 1978

[54] TWO PHASE ANTIPERSPIRANT COMPOSITIONS

[75] Inventor: David Lee Shelton, Cincinnati, Ohio

[73] Assignee: The Procter & Gamble Company, Cincinnati, Ohio

[21] Appl. No.: 745,723

[22] Filed: Nov. 29, 1976

[51] Int. Cl.$^2$ ............................................... A61K 7/34
[52] U.S. Cl. ................................ 424/66; 424/DIG. 5; 424/16; 424/25; 424/68
[58] Field of Search ................... 424/DIG. 5, 16, 25, 424/66

[56] References Cited

U.S. PATENT DOCUMENTS

| | | | |
|---|---|---|---|
| 2,087,161 | 7/1937 | Moore | 424/68 |
| 2,087,162 | 7/1937 | Moore | 424/68 |
| 2,732,327 | 1/1956 | Teller | 424/66 |
| 2,854,382 | 9/1958 | Grad | 423/462 |
| 2,933,433 | 4/1960 | Teller | 424/68 |
| 3,255,082 | 6/1966 | Barton | 424/68 |
| 3,259,545 | 7/1966 | Teller | 424/66 |
| 3,911,105 | 10/1975 | Papantoniou | 424/DIG. 5 |
| 3,929,986 | 12/1975 | Bouillon et al. | 424/DIG. 5 |
| 3,957,969 | 5/1976 | Fujiyama et al. | 424/DIG. 5 |
| 3,963,833 | 6/1976 | De Salva et al. | 424/DIG. 5 |
| 4,005,189 | 1/1977 | Reese et al. | 424/DIG. 5 |
| 4,010,253 | 3/1977 | Reese et al. | 424/DIG. 5 |
| 4,049,792 | 9/1977 | Elsnau | 424/DIG. 5 |

*Primary Examiner*—Dale R. Ore
*Attorney, Agent, or Firm*—Douglas C. Mohl; Richard C. Witte

[57] ABSTRACT

Stable, two phase antiperspirant stick compositions having (1) a substantially anhydrous antiperspirant phase comprising a water-insoluble, high melting point wax, a liquid emollient, and high levels of a particulate, antiperspirant active material and (2) a gel phase comprising a polyhydric alcohol gelled with either a fatty acid soap or a fatty acid amide. Such antiperspirant sticks provide effective antiperspirancy performance as well as desirable application characteristics.

10 Claims, No Drawings

TWO PHASE ANTIPERSPIRANT COMPOSITIONS

BACKGROUND OF THE INVENTION

The present invention relates to antiperspirant compositions in the form of solid sticks. The compositions herein comprise two phases, one an anhydrous waxy phase containing antiperspirant salts and the other an alcohol gel phase which can contain deodorant materials.

Antiperspirant compositions in stick form are known in the art. Single phase antiperspirant compositions have, for example, been disclosed in Taub; U.S. Pat. No. 1,984,669; issued Dec. 18, 1934 and Procter & Gamble; British Pat. No. 1,433,695; granted Aug. 25, 1976. Stick compositions of this type typically employ large amounts of waxy materials as the vehicle which delivers the antiperspirant active to the skin. Such stick products are stable and are especially effective for delivering large amounts of antiperspirant salts to the skin.

Attempts have been made to realize deodorant and antiperspirant sticks which deliver active ingredients to the skin via a vehicle which glides easily over skin surface and which imparts a cooling sensation to the skin during and after application. Soap/alcohol gels can provide such cosmetic benefits. However, incorporation of conventional astringent antiperspirant salts into such gels tends to interfere with the gel structure and render it less cosmetically desirable. To solve such compatability problems, alcohol gel sticks have been formulated using special additives such as lactate salts. (See, for example, Teller; U.S. Pat. No. 2,732,327, issued Jan. 24, 1956 and Slater; U.S. Pat. No. 2,900,306, issued Aug. 18, 1959). Some alcohol gel antiperspirant sticks have also been formulated in two phases with an inner core containing gel-compatable antiperspirant salts and an outer shell containing deodorant materials (See Bell, U.S. Pat. No. 2,970,083, issued Jan. 31, 1961).

Combinations of a conventional waxy antiperspirant composition with a soap/alcohol gel phase to form a two phase stick composition could enhance composition efficacy and improve composition cosmetic benefits. Such combination is, however, not made without certain difficulties. While each phase alone of such a stick composition is stable, contact between the two phases can cause destructive interaction between the two phases. The alcohol gel phase experiences syneresis, a bleeding or leaking of the gelled alcohol from the gel structure or matrix. Such leaked alcohol can interact with components of the waxy phase and can thus consume or physically separate the phases, thereby resulting in an unacceptable consumer product.

Given the state of the antiperspirant stick art as described above, there is a continuing need for new and useful antiperspirant stick compositions which provide both the stability and efficacy characteristics of waxy stick compositions and the desirable application characteristics of soap/alcohol gel compositions. Accordingly, it is an object of the present invention to provide a two phase antiperspirant stick with effective antiperspirancy performance and desirable application characteristics.

It is a further object of the present invention to provide such two phase antiperspirant sticks which are dimensionally stable.

It is a further object of the present invention to provide such two phase antiperspirant sticks which are not subject to destructive interfacial interaction.

It is a further object of the present invention to provide two phase antiperspirant sticks which can deliver both antiperspirant and deodorant materials to the skin simultaneously.

It has been surprisingly discovered that the above objective can be realized and superior two phase antiperspirant sticks provided by formulating a stick comprising an anhydrous antiperspirant phase utilizing particular amounts of certain types of waxes, emollients and antiperspirant actives and a gel phase formulated with particular amounts of certain polyhydric alcohols and gel-forming agents.

SUMMARY OF THE INVENTION

The present invention relates to antiperspirant compositions in the form of a two phase stick. Such compositions comprise from about 40 to 60% by weight of a substantially anhydrous antiperspirant phase and from about 40% to 60% by weight of a gel phase contiguous to the antiperspirant phase.

The antiperspirant phase of the two phase stick compositions contains from about 8 to 15% by weight of the antiperspirant phase of a high melting point wax, from about 20 to 50% by weight of the antiperspirant phase of a water-insoluble, liquid, non-hydrocarbon, organic emollient and from about 30 to 60% by weight of the antiperspirant phase of particulate astringent antiperspirant material. The high melting point wax utilized in the antiperspirant phase has a melting point between about 150° F. and 215° F.

The gel phase of the two phase stick composition contains from about 15 to 30% by weight of gel phase of a polyhydric aliphatic alcohol and from about 5 to 15% by weight of gel phase of a gel forming agent.

The polyhydric alcohol used in the gel phase contains from 2 to 4 carbon atoms and 2 or 3 hydroxyl groups. The gel forming agent can be either a sodium or potassium salt of a fatty acid having from 14 to 22 carbon atoms or a fatty acid amide containing from about 14 to 22 carbon atoms.

Preferred embodiments of the two phase stick compositions herein provide the antiperspirant phase in the form of a core with the gel phase surrounding the core. Preferred embodiments also include two phase sticks wherein the gel phase contains a monohydric alcohol component to provide a skin cooling sensation and a deodorant material to provide deodorant efficacy.

DETAILED DESCRIPTION OF THE INVENTION

The two-phase antiperspirant stick compositions of the present invention comprise A) an antiperspirant phase and B) a gel phase contiguous to the antiperspirant phase. Both of these essential components as well as optional components, composition preparation, and composition use are discussed in detail as follows:

ANTIPERSPIRANT PHASE

One essential component of the antiperspirant sticks herein is a solid waxy phase which provides the vehicle for the antiperspirant active ingredient. Such an antiperspirant phase of the type hereinafter described serves to deliver antiperspirant materials to the skin via a medium which does not feel runny, cold, or sticky and which provides the antiperspirant active in an especially effective undissolved particulate form.

The antiperspirant phase component of the stick compositions herein comprises from about 40 to 60%, preferably from about 45 to 55%, by weight of the total composition. The antiperspirant phase is solid (i.e., able to retain a rigid form at 20° C.) and is substantially anhydrous (i.e., comprises no more than about 1.0% by weight of antiperspirant phase of water). The antiperspirant phase essentially comprises a water-insoluble wax, a liquid organic emollient and particulate antiperspirant active material.

Water-Insoluble Wax

A high melting point, water-insoluble wax is the principal component of the antiperspirant phase of the stick compositions herein. It is believed that the high melting point wax provides a structure which can be sheared during application to the skin, thereby depositing layers of wax and antiperspirant active particles onto the skin.

The antiperspirant phase herein contains from about 8 to 15%, preferably from about 8 to 13%, by weight of antiperspirant phase of the water-insoluble wax materials. Maintenance of wax concentrations within these limits is essential for the realization of acceptable stick cosmetic characteristics. Such concentrations are also important in minimizing interaction between the antiperspirant phase and the contiguous gel phase.

Waxes employed as an essential component of the antiperspirant phase of the sticks herein are essentially water-insoluble (0.5% by weight in water at 80° F.). Such waxes have a melting point within the range of from about 150° F. to 215° F., preferably within the range of from about 170° F. to 210° F. Such waxes are referred to as high melting point waxes. Examples of suitable high melting waxes are beeswax, spermaceti, carnauba, bayberry, candelilla, montan, ozokerite, ceresin, paraffin, synthetic waxes such as Fisher-Tropsch waxes, and micro-crystalline wax. Preferred high melting waxes are ceresin, ozokerite, white beeswax and synthetic waxes.

Liquid Organic Emollient

A second essential component of the antiperspirant phase is a liquid organic non-hydrocarbon emollient. This emollient component serves to improve the cosmetic acceptability of the compositions herein by helping to impart a soft, supple character to the skin treated with the instant stick compositions.

The emollients used herein can be any non-toxic, non-irritating, non-hydrocarbon, organic material or mixtures thereof which is liquid at 20° C. and which is substantially water-insoluble (i.e. water solubility of from about 0.5 to 1.0% by weight in water at 20° C.). The emollient component comprises from about 20 to 50%, preferably from about 30 to 40%, by weight of the antiperspirant phase.

Suitable organic non-hydrocarbon emollients include fatty acid and fatty alcohol esters and water insoluble ethers. Examples of such emollients include isopropyl myristate, isopropyl palmitate, cetyl acetate, cetyl propionate, di-n-butyl phthalate, diethyl sebacate, diisopropyl adipate, ethyl carbomethyl phthalate, and the condensation product of about 14 moles of propylene oxide with one mole of butyl alcohol (Fluid AP ®). Preferred organic liquid emollients include isopropyl myristate, isopropyl palmitate, di-n-butyl phthalate, and Fluid AP ®. Especially preferred organic emollients include isopropyl myristate, isopropyl palmitate, and Fluid AP ®.

Suitable emollients for use herein also include nonvolatile polyorganosiloxane materials. Useful alcohol-soluble materials of this type can have the chemical structure:

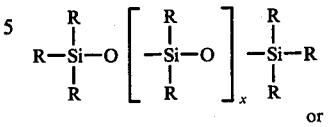

or

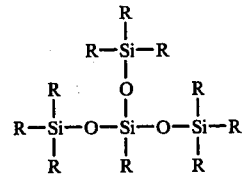

wherein the R groups can be the same or different and are selected from $C_1$–$C_4$ alkyl groups and phenyl groups, wherein x equals the number of repeating diorganosiloxy groups and wherein the viscosity of said organopolysiloxane is from about 9 to about 50 cs at 25° C. Examples of such organopolysiloxanes include DC-556 fluid, which is tris (trimethylsiloxy) phenylsilane and DC-225 fluid, a polydimethylsiloxane having a viscosity of 9.5 cs at 25° C., both marketed by Dow Corning Corporation. Preferred polysiloxane emollients include SWS-03314 marketed by Stauffer Chemical Company and UC-7207 marketed by Union Carbide Corporation.

Emollients including the liquid emollients suitable for use herein are described more fully in Balsam and Sagarin, Cosmetics Science and Technology, 2nd. Ed., Vol. 1, Wiley-Interscience, 1972, Chapter 2, pp. 27–104. This publication is incorporated herein by reference.

Particulate Antiperspirant Material

A third essential component of the antiperspirant phase of the present compositions comprises a particulate astringent antiperspirant material. Such antiperspirant active material, of course, imparts antiperspirancy efficacy to the antiperspirant stick compositions of the present invention.

Any aluminum astringent antiperspirant salt or aluminum and/or zirconium astringent complex in particulate form can be employed herein. Such salts and complexes are well known in the antiperspirant art. Salts useful as astringent antiperspirant salts or as components of astringent complexes include aluminum halides, aluminum hydroxyhalides, zirconyl oxyhalides, zirconyl hydroxyhalides and mixtures of these salt materials.

Aluminum salts of this type includes aluminum chloride and the aluminum hydroxyhalides having the general formula $Al_2(OH)_xQ_y \cdot XH_2O$ wherein Q is chlorine, bromine or iodine; wherein $x$ is 2 to 5 and $x+y = 6$ and $x$ and $y$ do not need to be integers; and wherein X is 1 to 6. Aluminum salts of this type can be prepared in the manner described more fully in Gilman, U.S. Pat. No. 3,887,692, issued June 3, 1975, incorporated herein by reference.

Zirconium salts useful in antiperspirant complexes include zirconium oxychloride [$ZrOCl_2 \cdot 8H_2O$], zirconium hydroxychloride [$ZrO(OH)Cl \cdot 3H_2O$] and the zirconium salts of the general formula $ZrO(OH)_{2-a} Cl_a \cdot nH_2O$ wherein $a$ is from about 1.5 to about 1.87 and $n$ is from 1 to about 7. Zirconium salts of this latte type are more fully described in Procter & Gamble, Belgium Pat. No. 825,146, published Aug. 4, 1975, said patent being incorporated herein by reference.

Several types of antiperspirant complexes utilizing the above antiperspirant salts are known in the art. For example, Luedders et al,; U.S. Pat. No. 3,792,068, issued Feb. 12, 1974 discloses complexes of aluminum, zirconium and amino acids such as glycine. Complexes such as those disclosed in this Luedders et al. '068 patent and other similar complexes are commonly known as ZAG. ZAG complexes useful herein are formed by (A) Co-dissolving in water
  (1) one part $Al_2(OH)_{6-m}Q_m$, wherin Q is an anion selected from the group consisting of chloride, bromide and iodide and $m$ is a number from about 0.8 to about 2.0;
  (2) $x$ parts $ZrO(OH)_{2-a}Q_a \cdot nH_2O$ where Q is chloride, bromide or iodide; wherein $a$ is from 1 to 2; where $n$ is from 1 to 7; and where x has a value of from about 0.16 to about 1.2;
  (3) $p$ parts neutral amino acid selected from the group consisting of glycine, dl-tryptophane, dl-$\beta$-phenylalanine, dl-valine, dl-methionine and $\beta$-alanine, and where $p$ has a value of from about 0.06 to about 0.53; (B) Co-drying the resultant mixture to a friable solid; and
(C) Reducing the resultant dried inorganic-organic antiperspirant complex to particulate form.

The preferred aluminum compound for preparation of such ZAG type complexes is aluminum chlorhydroxide of the empirical formula $Al_2(OH)_5Cl \cdot 2H_2O$. The preferred zirconium compounds for preparation of such ZAG-type complexes are zirconyl hydroxychloride having the empirical formula $ZrO(OH)Cl \cdot 3H_2O$ and the zirconyl hydroxyhalides of the empirical formula $ZrO(OH)_{2-a}Cl_a \cdot nH_2O$ wherein $a$ is from 1.5 to 1.87 and $n$ is from about 1 to 7. The preferred amino acid for preparing such ZAG-type complexes is glycine of the formula $CH_2(NH_2)COOH$. (Salts of such amino acids can also be employed in such antiperspirant complexes.)

A wide variety of other types of anitperspirant complexes are also known in the art. For example, Siegal; U.S. Pat. No. 3,903,258, issued Sept. 2, 1975 discloses a zirconium aluminum complex prepared by reacting zirconyl chloride with aluminum hydroxide and aluminum chlorhydroxide. Rubino; U.S. Pat. No. 3,979,510, issued Sept. 7, 1976 discloses an antiperspirant complex formed from certain aluminum compounds, certain zirconium compounds and certain complex aluminum buffers. Rubino; U.S. Pat. No. 3,981,896, issued Sept. 21, 1976 discloses an antiperspirant complex prepared from an aluminum polyol compound, a zirconium compound and an organic buffer. Mecca; U.S. Pat. No. 3,970,748, issued July 20, 1976 discloses an aluminum chlorhydroxy glycinate complex of the approximate general formula $[Al_2(OH_4)Cl][H_2CNH_2COOH]$. All of these patents are incorporated herein by reference.

Of all the above types of antiperspirant actives, preferred compounds include the 5/6 basic aluminum salts of the empirical formula $Al_2(OH)_5Cl \cdot 2H_2O$; mixtures of $AlCl_3 \cdot 6H_2O$ and $Al_2(OH)_5Cl \cdot 2H_2O$ with aluminum chloride to aluminum hydroxychloride weight ratios of up to about 0.5; ZAG type complexes wherein the zirconium salt is $ZrO(OH)Cl \cdot 3H_2O$; the aluminum salt is $Al_2(OH)_5Cl \cdot 2H_2O$; and the amino acid is glycine and ZAG-type complexes wherein the zirconium salt is $ZrO(OH)_{2-a}Cl_a \cdot nH_2O$ with a ranging from about 1.5 to 1.87 and $n$ ranging from about 1 to 7; the aluminum salt is $Al_2(OH)_5Cl \cdot 2H_2O$; and the amino acid is glycine.

The antiperspirant phase of the present stick compositions contains from about 30 to 60%, preferably from about 40 to 50%, by weight of the antiperspirant phase of the particulate astringent antiperspirant material. Such particulate antiperspirant material is preferably impalpable, i.e. has particle sizes ranging from about 1 to about 100 microns, more preferably from about 1 to about 50 microns. The antiperspirant active material herein is preferably alcohol insoluble.

Optional Antiperspirant Phase Components

The antiperspirant phase of the instant stick compositions can contain a variety of optional ingredients suitable for improving composition efficacy, stability, cosmetics and/or aesthetics. Such optional antiperspirant phase components include low melting point waxes to adjust stick cosmetics, inert filler material to improve composition stability and cosmetics, perfumes, dyes, coloring agents, preservatives and the like.

A highly preferred optional component of the waxy antiperspirant phase is an additional wax material having a melting point of from about 100° F. up to about 150° F. Such optional waxes are referred to herein as low melting point waxes. The low melting point wax component can be used as an adjunct to the high melting point wax to provide improved emolliency and to enhance the structural integrity of the waxy antiperspirant phase. The low melting point wax can also be used to adjust the fell of the stick compositions herein. One skilled in the art will easily be able to make a product which feels more brittle, soft, slippery, sticky, rough, etc., by blending various suitable low melting point waxes with the essentially present high melting point waxes.

Examples of useful low melting point waxes include fatty acids containing from about 8 to about 20 carbon atoms, fatty alcohols containing from about 8 to about 20 carbon atoms, silicone waxes and glycerol monostearate. Especially preferred materials of this type are the $C_8$ to $C_{20}$ fatty acids and $C_8$ to $C_{20}$ fatty alcohols. The most preferred low melting point waxes are cetyl alcohol, stearyl alcohol, myristyl alcohol, lauryl alcohol and glycerol monostearate.

If present, the low melting point wax component generally comprises from about 2 to about 20%, more preferably from about 5 to about 15%, by weight of the antiperspirant phase.

Another preferred optional component for possible use in the antiperspirant phase of the stick compositions herein is an inert filler material. Such filler materials also serve to enhance the structural integrity of the antiperspirant phase herein and serve to improve composition cosmetics.

Useful inert particulate filler materials include talc; colloidal silica, e.g., Cab-O-Sil (Cabot Corp.), a pyrogenic silica having an average particulate diameter between about 0.001 and 0.03 microns as disclosed in British Pat. No. 987,301 and British Pat. No. 1,167,173, and finely divided hydrophobic clays such as the reaction product of a clay such as bentonite and dimethyldistearyl ammonium chloride, such treated clays being marketed under the tradename "BENTONE" by NL Industries. Such clay materials are described more fully in British Pat. No. 1,167,173.

If present, the inert particulate filler material generally comprises from about 0.5 to 5.0% by weight of the waxy antiperspirant phase of the present stick compositions.

The antiperspirant phase herein can also contain minor amounts i.e., from about 0.1 to 1.5% by weight of antiperspirant phase, of conventional additives such as dyes, perfumes, pigments, coloring agents, etc. In selecting such ingredients only small amounts of hydrophilic materials shall be used in addition to the active material. Preferably, less than about 5% of the antiperspirant phase, in addition to the antiperspirant materials, is soluble in water.

GEL PHASE

The second essential component of the antiperspirant sticks of this invention is a gel phase formed from certain polyhydric alcohols and certain gel-forming agents. This gel phase comprises from about 40 to 60 %, preferably from about 45 to 55%, by weight of the total antiperspirant stick compositions herein.

The gel phase is maintained in a position contiguous to the waxy antiperspirant phase of the stick compositions herein. The primary purpose of the gel phase of the sticks herein is to improve the glidability and ease of application of the instant stick compositions onto the skin. Optionally the gel phase herein can also act as a carrier for deodorant materials and for materials such as monohydric alcohols which impart a desirable cooling, moist sensation to the skin upon application. Even though the gel phase herein is maintained in contact with the anhydrous waxy antiperspirant phase, selection of particular gel and antiperspirant phase components and component concentrations insures minimal interaction between gel and antiperspirant phases at their interface.

Polyhydric Alcohol

One essential component of the gel phase of the present antiperspirant stick compositions is a polyhydric aliphatic alcohol containing from 2 to 4 carbon atoms and from 2 to 3 hydroxyl groups. This polyhydric alcohol is the medium which is "gelled" to form the gel phase of the stick compositions herein. The polyhydric alcohol component of the gel phase comprises from about 10 to 92%, preferably from about 15 to 30%, by weight of the gel phase.

Suitable polyhydric alcohol for use in the gel phase herein include ethylene glycol, propylene glycol, trimethylene glycol, glycerine, 1,3-butane-diol and 1,4 butane-diol. The most preferred polyhydric alcohol is propylene glycol.

Gel Forming Agents

The second essential component of the gel phase of the antiperspirant stick compositions herein is a gel forming agent which is added to the alcoholic components of the gel phase to form the desired gel material. The gel forming agents used herein can be the sodium and potassium salts (i.e. soaps) of fatty acids containing from about 14 to 22 carbon atoms or can also be fatty acid amides containing from about 14 to 22 carbon atoms.

Gel forming agents generally comprise from about 5 to 15% by weight of the gel phase herein. When soaps are utilized as the gel forming agent, the gel forming agent preferably comprises from about 7 to 10% by weight of the gel phase. When amides are employed as the gel forming agent, the concentration of the gel forming agent preferably ranges from about 10 to 15% by weight of the gel phase. If gel forming agent concentrations lower than those specified are employed, the gels formed tend to be dimensionally unstable and tend to interact with the contiguous waxy antiperspirant phase. If concentrations of gel forming agents above those specified are utilized, the gels formed tend to be too hard and do not exhibit desirable glide and application characteristics. By utilizing gel-promoting agents of the particular type described and in the concentrations specified, gel phases can be formulated which exhibit minimal undesirable interfacial interaction and which exhibit the cosmetically desirable application properties.

The fatty acid portion of the soap or amide gel forming agents should be essentially pure saturated or unsaturated higher fatty acids having a $C_{14}$ to $C_{22}$ backbone. Suitable mixtures of such acids can be employed provided that such mixtures are free from significant proportions of other fatty acids of higher or lower chain length which substantially adversely affect or neutralize the desired gel forming effects.

Examples of fatty acids useful in synthesizing the gel forming agents herein include myristic, palmitic, stearic, oleic, linoleic, linolenic, arachidic, behenic, margaric acids and the mixtures of such acids naturally occuring in fats, oils, waxes and rosins. Naturally occuring sources of such fatty acids include coconut oil, tallow, lanolin, fish oil, beeswax, palm oil, sesame oil, peanut oil, olive oil, palm kernel oil, cottonseed oil, soybean oil, corn oil, babassu oil, rapeseed oil, rosin acids, abietic acid, and greases. Conventional fractionation and/or hydrolysis techniques can be employed if necessary to obtain the requisite types of fatty acids from such materials.

Preferred fatty acid soap type gel forming agents include sodium stearate, sodium palmitate, potassium stearate, potassium palmitate and sodium myristate. Preferred fatty acid-amide type gel forming agents include stearamide, palmitamide and myristamide. The most preferred gel forming agent is sodium stearate.

Optional Gel-Phase Components

The gel phase of the instant stick compositions can contain a variety of optional ingredients suitable for improving composition efficacy, stability, cosmetics and/or aesthetics. Such optional gel phase components include monohydric alcohols to improve composition cosmetics, deodorant materials, alcohol evaporation retardants, and anti-syneresis agents, perfumes, dyes, pigments, coloring agents and the like.

A highly preferred optional component of the gel phase is a monohydric alcohol which serves to impart a cosmetically desirably cooling sensation to the skin. Monohydric alcohols of this type contain one to four carbon items and can be primary, secondary or tertiary. Examples of suitable monohydric alcohols include methanol, ethanol, isopropanol, n-propanol, n-butanol, isobutanol and tert-butyl alcohol. Preferred monohydric alcohols are ethanol and isopropanol.

While monohydric alcohols can provide a desirable cosmetic cooling benefit for the antiperspirant stick compositions herein, inclusion of a monohydric alcohol component can also lead to several types of stick composition instability problems. Monohydric alcohols tend to provide dimensional instability of the gel phase and tend to cause the gel phase to become sticky or tacky. Monohydric alcohols can also bleed from the gel phase (i.e. cause the gel phase to exhibit syneresis). When this occurs, the gel phase tends to interact with components of the anhydrous waxy antiperspirant phase of the stick compositions herein. Such interaction can lead to destruction of the structural integrity of the two phase stick compositions.

It has been surprisingly discovered that such problems can be minimized and that monohydric alcohols can be successfully incorporated into the gel phase of the stick compositions herein provided certain concentration limits for the essential gel phase components are observed. When monohydric alcohols are employed, it has been found that the weight ratio of polyol to gel forming agent must exceed about 2.45. When polyol and gel forming agents are present in this ratio, monohydric alcohols can be incorporated into the gel phase in amounts of from about 10 to 72%, preferably from about 40 to 70%, by weight of the gel phase.

When monohydric alcohols are employed, another highly preferred optional component of the gel phase is a material which helps retard alcohol evaporation and which acts as an anti-syneresis agent. Especially preferred materials of this type are cellulose derivatives such as carboxyalkylcelluloses and hydroxyalkylcelluloses. Especially preferred materials of this type are hydroxypropylcellulose compounds having the chemical formula:

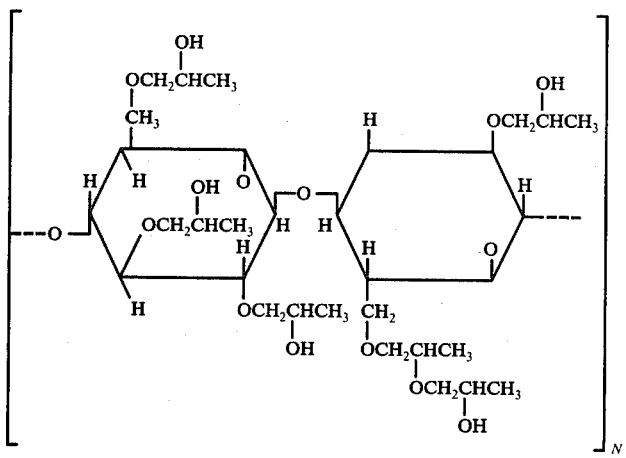

and wherein N is sufficiently large such that the total molecular weight of the material ranges from about 60,000 to about 1,000,000. Such materials are sold under the tradename of Klucel ® by Hercules Incorporated. If present, such alcohol evaporation retarding agents and anti-syneresis agents comprise from about 0.1 to 5.0% by weight of the gel phase.

Another highly preferred optional ingredient of the gel phase herein is a conventional deodorant material. Suitable deodorants include bacteriostatic quaternary ammonium compounds such as cetyltrimethylammonium bromide and cetyl pyridinium chloride, salts of monohydroxy-benezene sulfonic acids and mono or divalent metals such as zinc phenolsulfonate, halogenated dihydroxydiphenyl methanes, and derivatives of 1,3-diphenyl-urea where one or more of the hydrogen atoms on the phenyl rings are replaced with halogens, i.e. tri-chlorocarbanilide.

If present, deodorants generally comprise from about 0.1 to 1.0% by weight of the gel phase. Stick compositions which contain deodorant in the gel phase are, of course, especially desirable since both antiperspirant and deodorant efficacy can thus be provided by the same stick product.

Conventional optional ingredients such as perfumes, dyes, pigments, coloring agents and the like can also be added to the gel phase. If present such minor additions comprise from about 0.1 to 1.5% by weight of the gel phase.

Small amounts of water can be added to the gel phase. The amount of water added should, however, be limited to less than 5%. Water in the gel phase at concentrations exceeding 5% tends to dissolve the antiperspirant active in the antiperspirant phase and thereby to aggravate interfacial interaction and stick degradation.

COMPOSITION PREPARATION

The waxy antiperspirant and gel phases of the present stick compositions are prepared separately in their desired geometric configurations. The waxy antiperspirant phase of the present compositions is generally prepared by heating the solid waxes and liquid emollient in a suitable container while gently stirring. When the wax or waxes are melted and mixed thoroughly with the emolient, the antiperspirant active ingredient is mixed and dispersed in the melt. The optional ingredients can then be added or the melt can be cooled to a temperature above the solidification point before adding additional ingredients. Care should be taken in preparing the antiperspirant phase to avoid use of any materials or procedures which might introduce free moisture into the composition above the substantially anhydrous level.

The gel phase of the present composition can be prepared by admixing the essential and optional gel phase components together in such a manner as to produce a thickened, stable gel. In a preferred mode of gel preparation, the monohydric alcohol and the polyhydric alcohol, are mixed together in a reflux vessel with moderate agitation. Upon heating the mixture to boiling, the gel-forming agents can be added under continuing refluxing and agitation until the gel promoting agent fully dissolves. Optional ingredients such as dyes, deodorants and perfumes can then be added. Refluxing and moderate agitation is contained until boiling reoccurs, if there has been an appreciable temperature drop due to the addition of the optional materials. The molten mixture can then be placed in a mold device such that the mixture is allowed to gel into a dimensionally stable mass of the desired geometric configuration.

Once prepared, the waxy antiperspirant and gel phases of the compositions herein can be joined or combined by any suitable means or in any suitable device so that a single antiperspirant stick is formed. In the stick product, the waxy antiperspirant and gel phases should be contiguous such that, in a cross section of the stick, both phases are exposed in a single continuous application surface.

In a most preferred embodiment the waxy antiperspirant phase is formed as a core of any suitable shape and the gel phase is formed as a shell surrounding the waxy antiperspirant phase. Most preferably the antiperspirant phase core and the surrounding gel phase shell are in the form of concentric cylinders. To prepare dual phase cylindrical stick compositions of this type, the molten gel phase is added to appropriate mold containers wherein provision has been made for the subsequent addition of the antiperspirant core phase. Such containers can comprise a cylinder with inert core equipped with means for removing the core. The molten gel is added to the annular space and allowed to cool and solidify. The inert core is then removed leaving a central cylindrical cavity into which the molten antiperspirant core material can be added to form the core phase of the instant two-phase antiperspirant sticks.

COMPOSITION USE

The two-phase antiperspirant sticks of the present invention are used to inhibit axillary perspiration in the same manner as any conventional antiperspirant stick composition. The present stick compositions can be easily applied to the skin leaving little or no perceptible residue. Such stick further provides cosmetically desirable application characteristics such as glidability and coolness not generally provided by single phase stick compositions.

The two-phase antiperspirant compositions herein are generally marketed in combination with some type of conventional packaging or dispensing means. Such means can include handles, wrappers, tubes, extruding devices and the like.

The two-phase antiperspirant sticks of the present invention are illustrated by the following examples:

EXAMPLE I

A two-phase antiperspirant stick of the following composition is prepared.

| Component | | Wt.% |
|---|---|---|
| A. Antiperspirant Core | | 50% |
| Ingredient | Percent by Weight | |
| Ozokerite wax | 8.5% | |
| Cetyl alcohol | 8.5% | |
| Isopropyl palmitate | 35.0% | |
| Aluminum chlorhydroxide particles [Al$_2$(OH)$_5$Cl . 2H$_2$O] | 43.5% | |
| Perfume | 0.5% | |
| *Cab-O-Sil (grade M-5) | 4.0% | |
| | 100.0% | |
| B. Gel-Phase Shell | | 50% |
| Ingredient | Percent by Weight | |
| Ethanol | 72% | |
| Sodium Stearate | 7.5% | |
| Propylene glycol | 17.00% | |
| FD&C Blue #1 (coloring) | 0.25% | |
| Perfume | 0.8% | |
| Water | 2.45% | |
| | 100.00% | |
| | | 100% |

*A pyrogenic silica (Cabot Corp.) having a particulate diameter between about 0.001 and 0.03 microns as disclosed in British Patent 987,301 and British Patent 1,167,173.

In Example I, the stick is prepared by charging a steel vessel equipped with a reflux condenser with the ethanol and the propylene glycol, and then is heated with moderate agitation until the mixture begins to boil and reflux. Thereafter, the sodium stearate is added. The heating and agitation is continued until the sodium stearate is completely dissolved. Next, the cetyl pyridinium chloride, the FD&C Blue #1, and the perfume are added while maintaining the agitation and refluxing. The molten gel material is then poured into the annular space of a suitable cylindrical mold equipped with removable inert cylindrical core piece and is allowed to solidfy. Thereafter the inert core piece is removed leaving a cylindrical cavity.

The wax, cetyl alcohol, and IPP are charged to another steel vessel, and are heated with mild agitation until the wax, cetyl alcohol and IPP are well intermixed. Next, the aluminum chlorhydroxide is stirred into the composition and is dispersed therein. This mixture is then allowed to cool to just above the solidification temperature at which point the perfume is stirred into the mixture. The mix is finally poured into the cylindrical cavity of the gel phase shell and allowed to solidify.

The stick so produced is an effective antiperspirant composition in the form of a two-phase stick. The stick exhibits minimal syneresis and interfacial interaction and provides cosmetically desirable application characteristics when applied to the skin.

Sticks of substantially similar physical/cosmetic character and antiperspirant effectiveness are realized when in the Example I stick the isopropyl palmitate is replaced with an equivalent amount of isopropyl myristate, cetyl acetate, cetyl propionate, di-n-butyl phthalate, diethyl sebacate, diisopropyl adipate, ethyl carbomethyl phthalate, Fluid AP ® (Butyl alcohol condensed with about 14 moles of propylene oxide) or DCC-225 Fluid (dimethyl siloxane polymer of viscosity 9.5 cs. at 25° C. marketed by Dow Corning Corp.).

Compositions of substantially similar physical/cosmetic character and antiperspirant effectiveness are realized when in the Example I stick the sodium stearate is replaced with an equivalent amount of sodium palmitate, sodium myristate, potassium palmitate or potassium stearate.

EXAMPLE II

A two-phase antiperspirant stick of the following composition is prepared:

| Component | | Wt.% |
|---|---|---|
| A. Antiperspirant Core | | 50% |
| Ingredient | Percent by Weight | |
| Ozokerite wax | 8.5% | |
| Stearyl alcohol | 10.0% | |
| Fluid AP ® (Propylene oxide/ butyl alcohol condensate) | 35.9% | |
| *ZAG powder antiperspirant | 45.6% | |
| | 100.0% | |
| B. Gel-Phase Shell | | 50% |
| Ingredient | Percent by Weight | |
| Sodium stearate | 7.0% | |
| Propylene glycol | 91.94% | |
| FD&C Blue #1 (coloring) | 0.26% | |
| Perfume | 0.80% | |
| | 100.00% | |

-continued

| Component | Wt.% |
|---|---|
| | 100% |

*ZAG is a complex formed from ZrO(OH)Cl . 3H$_2$O; Al$_2$(OH)$_5$Cl . 2H$_2$O and glycine in accordance with Luedders et al, U.S. Pat No. 3,792,068, issued Feb. 12, 1974. Average particle size = 25 microns.

Such a stick is prepared in a manner similar to that described in Example I. The stick so produced is an effective antiperspirant composition in the form of a two-phase stick. The composition exhibits minimal interfacial interaction and glides easily onto the skin during application.

Stick compositions of substantially similar physical/cosmetic character and antiperspirant effectiveness are realized when in the Example II stick composition the ozokerite wax is replaced with an equivalent amount of ceresin, white beeswax or carnuba wax.

Compositions of substantially similar physical/cosmetic character and antiperspirant effectiveness are realized when in the Example II composition the propylene glycol is replaced with an equal amount of glycerine, ethylene glycol, trimethylene glycol, 1,3-butane diol or 1,4-butane diol.

EXAMPLE III

A two-phase antiperspirant stick composition of the following composition is prepared.

| Component | | Wt.% |
|---|---|---|
| A. Antiperspirant Core | | 55% |
| Ingredient | Percent by Weight | |
| Carnuba wax | 10.0% | |
| Beeswax | 5.0% | |
| Stearyl alcohol | 7.0% | |
| Isopropyl myristate | 34.0% | |
| Aluminum chlorhydroxide Aluminum chloride mixture (ACH/AC wt. ratio = 3:1) | 40.0% | |
| Perfume | 1.0% | |
| Bentone 38® | 3.0 % | |
| | 100.0% | |
| B. Gel-Phase Shell | | 45% |
| Ingredient | Percent by Weight | |
| N-butanol | 60.55% | |
| Stearamide | 10.0% | |
| 1,3-butane diol | 27.0% | |
| FD&C Blue #1 (coloring, 0.5% aqueous solution) | 0.15% | |
| Zinc Phenolsulfonate (deodorant) | 1.0% | |
| Klucel® (antisynersis agent) | 0.5% | |
| Perfume | 0.8% | |
| | 100.0% | |
| | | 100% |

Such a stick is prepared in a manner similar to that described in Example I. The stick so produced is an effective antiperspirant/deodorant composition in the form of a two-phase stick. The composition exhibits minimal interfacial interaction and provides a cooling sensation when applied to the skin.

Stick compositions of substantially similar physical/cosmetic character and antiperspirant/deodorant effectiveness are realized when in the Example III stick compositions the n-butanol is replaced by an equivalent amount of methanol, ethanol, isopropanol, n-propanol, isobutanol, or tert-butyl alcohol.

Stick compositions of substantially similar physical/cosmetic character and antiperspirant/deodorant effectiveness are realized when, in the Example III composition, the stearamide gel forming agent is replaced with an equivalent amount of palmitamide or myristamide.

Stick compositions of substantially similar physical/cosmetic character and antiperspirant/deodorant effectiveness are realized when, in the Example III composition, the stearyl alcohol is replaced with an equivalent amount of cetyl alcohol, myristyl alcohol, lauryl alcohol or glycerol monostearate.

Stick compositions of substantially similar physical/cosmetic character and antiperspirant/deodorant effectiveness are realized when, in the Example III composition, the aluminum chlorhydroxide/aluminum chloride mixture is replaced with an equivalent amount of a particulate antiperspirant active material selected from the group consisting of ZAG complexes wherein the zirconium compound is $ZrO(OH)_{2-a}Cl_a \cdot nH_2O$ with $a = 1.5$ to $1.87$ and $n = 1$ to $7$; the aluminum compound is $Al_2(OH)_5Cl \cdot 2H_2O$ and the amino acid compound is glycine.

Interfacial Interaction Evaluation

As noted above, certain minimum amounts of (1) gel forming agent in the gel phase and (2) water insoluble, high melting point wax in the antiperspirant phase are essential to the realization of two-phase antiperspirant sticks which are not subject to degradation by interfacial interaction. The importance of such concentration limitations can be demonstrated by formulating compositions with varying amounts of each component and observing such compositions after a two month storage at 70° F. Those compositions subject to interfacial interaction are identified by the presence of a liquid runoff present in the bottom of the container holding the two-phase sticks.

Several stick compositions are selected for such interfacial interaction evaluation. The compositions tested are those described in Table I.

TABLE I

| Component | | | | | | | | | | |
|---|---|---|---|---|---|---|---|---|---|---|
| Gel Phase (50% by weight) Ingredient | Percent by weight of Gel Phase | | | | | | | | | |
| | A | B | C | D | E | F | G | H | I | J |
| Sodium stearate | 5 | 6 | 6 | 7 | 7 | 7 | 7 | 8 | 8 | 9 |
| Ethanol | 80 | 77 | 12 | 74 | 31 | 70 | 32 | 70 | 40 | 67 |
| Propylene Glycol | 13 | 15 | 80 | 17 | 60 | 21 | 60 | 21 | 50 | 22 |
| Optionals | 2 | 2 | 2 | 2 | 2 | 2 | 2 | 2 | 2 | 2 |
| Antiperspirant Phase (50% by weight) Ingredient | Percent by weight of A/P Phase | | | | | | | | | |
| | A | B | C | D | E | F | G | H | I | J |
| Ozokerite Wax | 9 | 8 | 7 | 6 | 7 | 8 | 9 | 10 | 11 | 12 |
| Isopropyl Palmitate | 26 | 32 | 38 | 44 | 47 | 41 | 35 | 27 | 23 | |
| Aluminum Chlorhydroxide | 55 | 50 | 45 | 40 | 35 | 35 | 40 | 45 | 50 | 55 |
| Optionals | 10 | 10 | 10 | 10 | 10 | 10 | 10 | 10 | 10 | 10 |
| | Experienced Interfacial Interaction | | | | | Did not Experience Interfacial Interaction | | | | |

As can be seen from the above Table I, compositions A through E exhibit interfacial interaction while compositions F through J do not exhibit such degradation. Compositions F–J represent compositions of the present invention inasmuch as these compositions contain more than the essential minimum amounts of both the gel forming agent in the gel phase and the water insoluble, high melting point wax in the antiperspirant phase. Compositions A–E, although perhaps containing more than the essential minimum amount of one of these two components, do not contain a sufficient amount of both components and thereby are subject to interfacial interaction.

What is claimed is:

1. An antiperspirant composition in the form of a two-phase stick, said composition comprising:
   (A) from about 40 to 60% by weight of the composition of a solid, substantially anhydrous antiperspirant phase comprising
      I. from about 8 to about 15% by weight of the antiperspirant phase of a water-insoluble high melting wax which has a melting point of from about 150° F. to about 215° F.
      II. from about 20 to about 50% by weight of the antiperspirant phase of a water-insoluble liquid, organic, non-hydrocarbon emollient; and
      III. from about 30 to about 60% by weight of the antiperspirant phase of a solid particulate astringent antiperspirant material; and,
   (B) from about 40 to 60% by weight of the composition of a gel phase contiguous to said solid antiperspirant phase, said gel phase comprising
      I. from about 10 to 92% by weight of the gel phase of a polyhydric aliphatic alcohol containing from 2 to 4 carbon atoms and from 2 to 3 hydroxy groups; and
      II. from about 5 to 15% by weight of the gel phase of a gel forming agent selected from the group consisting of sodium salt of a fatty acid containing from 14 to about 22 carbon atoms and potassium salt of a fatty acid containing from about 14 to about 22 carbon atoms.

2. A composition in accordance with claim 1 wherein the gel phase additionally contains from about 10 to 72% by weight of gel phase of a monohydric alcohol selected from the group consisting of methanol, ethanol, isopropanol, n-propanol, n-butanol, isobutanol and tert-butyl alcohol and wherein the weight ratio of polyhydric alcohol to gel-forming agent in the gel phase exceeds about 2.45.

3. A composition in accordance with claim 2 wherein the antiperspirant phase comprises a core and the gel phase comprises a shell surrounding said antiperspirant phase core.

4. A composition in accordance with claim 3 wherein
   (A) the high melting wax comprises from about 8 to 13% by weight of the antiperspirant phase and is selected from the group consistiong of beeswax, spermaceti, carnauba, bayberry, candelilla, montan, ozokerite, cersin, paraffin, a Fisher-Tropsch wax and a microcrystalline wax;
   (B) the organic emollient comprises from about 30 to 40% by weight of the antiperspirant phase and is selected from the group consisting of isopropyl myristate, isopropyl palmitate, cetyl acetate, cetyl propionate, di-n-butyl phthalate, diethyl sebacate, diisopropyl adipate, ethyl carbomethyl phthalate, the condensation product of about 14 moles of propylene oxide with 1 mole of butyl alcohol, and a polydimethylsiloxane having a viscosity of from about 9 to 50 cs. at 25° C.;
   (C) the particulate antiperspirant material comprises from about 40 to 50% by weight of the antiperspirant phase and is selected from the group consisting of
      (i) aluminum hydroxyhalides of the empirical formula $Al_2(OH)_xQ_y.XH_2O$ wherein Q is selected from the group consisting of chlorine, bromine and iodine, wherein X is from 2 to 5 and $x + y = 6$ and wherein X is 1 to 6; and
      (ii) zirconium/aluminum/amino acid complexes which contain
         (a) one part of an aluminum compound of the formula $Al_2(OH)_{6-m}Q_m.YH_2O$ wherein Q is selected from the group consisting of chloride, bromide and iodide; $m$ is a number from about 0.8 to 2.0 and Y is 1 to 6;
         (b) $x$ parts of a zirconium compound of the formula $ZrO(OH)_{2-a}Q_a.nH_2O$ wherein Q is selected from the group consisting of chloride, bromide and iodide; wherein $a$ is from 1 to 2, wherein $n$ is from 1 to 7 and wherein $x$ is from about 0.16 to about 1.2; and
         (c) $p$ parts neutral amino acid selected from the group consisting of glycine, dl-tryptophane, dl-$\beta$-phenylalanine, dl-valine, dl-methionine and $\beta$-alanine, and wherein $p$ has a value of from about 0.06 to about 0.53;
   (D) the polyhydric aliphatic alcohol comprises from about 15 to 30% by weight of the gel phase and is selected from the group consisting of ethylene glycol, propylene glycol, trimethylene glycol, glycerine, 1,3-butanediol and 1,4-butane diol; and
   (E) the monohydric alcohol comprises from about 40 to 70% by weight of the gel phase and is selected from the group consisting of ethanol and isopropanol.

5. A composition in accordance with claim 4 wherein the gel-forming agent comprises from about 7 to 10% by weight of the gel phase and is selected from the group consisting of sodium stearate, sodium palmitate, sodium myristate, potassium stearate and potassium palmitate.

6. A composition in accordance with claim 4 wherein the antiperspirant core contains an additional component selected from the group consisting of
   (A) from about 2 to 20% by weight of antiperspirant core of a low melting wax having a melting point of from about 100° F. up to about 150° F.;
   (B) from about 0.5 to 5% by weight of antiperspirant core of an inert filler material; and
   (C) combinations of both said low melting wax and said inert filler.

7. A composition in accordance with claim 4 wherein the gel phase shell contains an additional component selected from the group consisting of
   (A) from about 0.1 to 1.0% by weight of gel phase shell of a deodorant material;
   (B) from about 0.1 to 5.0% by weight of gel phase shell of an antisyneresis/evaporation retardant selected from the group consisting of carboxyalkylcellulose and hydroxyalkylcellulose; and
   (C) combinations of both said deodorant material and said antisyneresis/evaporation retardant.

8. A composition in accordance with claim 4 wherein
   (A) the high melting wax is selected from the group consisting of ceresin, beeswax, ozokerite and synthetic wax;
   (B) the emollient is selected from the group consisting of isopropyl myristate, isopropyl palmitate, the condensation product of about 14 moles of propylene oxide with butyl alcohol and a polydimethylsiloxane having a viscosity of from about 9 to 50 cs. at 25° C.;

(C) the antiperspirant material is in impalpable particulate form and is selected from the group consisting of
  (i) $Al_2(OH)_5Cl.2H_2O$
  (ii) mixtures of $AlCl_3.6H_2O$ and $Al_2(OH)_5Cl.2H_2O$ in an aluminum chloride to aluminum hydroxychloride weight ratio of up to 0.5;
  (iii) zirconium/aluminum/glycine complexes containing about one part $Al_2(OH)_5Cl.2H_2O$; $x$ parts of $ZrO(OH)Cl.3H_2O$ and $p$ parts glycine wherein $x$ is from about 0.16 to 1.2 and $p$ is from about 0.06 to 0.53; and
  (iv) zirconium/aluminum/glycine complexes containing about one part $Al_2(OH)_5Cl.2H_2O$; $x$ parts of $ZrO(OH)_{2-a}Cl_a nH_2O$; and $p$ parts glycine wherein $a$ is from about 1.5 to 1.87, $n$ is 1 to 7, $x$ is from about 0.16 to 1.2 and $p$ is from about 0.06 to 0.53;
(D) the polyhydric alcohol propylene glycol; and
(E) the gel forming agent comprises from about 7 to 10% by weight of the gel phase and is selected from the group consisting of sodium stearate, sodium palmitate, sodium myristate, potassium stearate and potassium palmitate.

9. A composition in accordance with claim 8 which contains an additional component selected from the group consisting of
  (A) from about 5 to 15% by weight of the antiperspirant core of low melting wax present in the antiperspirant core, said low melting wax being selected from the group consisting of cetyl alcohol, stearyl alcohol, myristyl alcohol, lauryl alcohol and glycerol monostearate;
  (B) from about 0.5 to 5% by weight of the antiperspirant core of an inert filler present in said antiperspirant core, said filler being selected from the group consisting of talc, a colloidal silica and a hydrophobic clay;
  (C) from about 0.1 to 5.0% by weight of the gel phase shell of an anti-syneresis agent present in said gel phase shell, said anti-syneresis agent comprising hydroxypropylcellulose compounds having molecular weights ranging from about 60,000 to 1,000,000;
  (D) from about 0.1 to 1.0% by weight of the gel phase shell of a deodorant material present in said gel phase shell, said deodorant material being selected from the group consisting of a bacteriostatic quaternary ammonium compound, a metal salt of monohydroxybenzene sulfonic acid, a halogenated dihydroxydiphenyl methane and a derivative of 1,3-diphenyl-urea having one or more hydrogen atoms replaced with halogen; and
  (E) various combinations of said additional components.

10. A composition in accordance with claim 1 wherein the particulate antiperspirant material comprises a zirconium/aluminum/amino acid complex containing
  (a) one part of an aluminum compound of the formula $Al_2(OH)_{6-m}Q_m.YH_2O$ wherein Q is selected from the group consisting of chloride, bromide and iodide; $m$ is a number from about 0.8 to 2.0 and Y is 1 to 6;
  (b) $x$ parts of a zirconium compound of the formula $ZrO(OH)_{2-a}Q_a nH_2O$ wherein Q is selected from the group consisting of chloride, bromide and iodide; wherein $a$ is from 1 to 2, wherein $n$ is from 1 to 7 and wherein $x$ is from about 0.16 to about 1.2; and
  (c) $p$ parts neutral amino acid selected from the group consisting of glycine, dl-tryptophane, dl-$\beta$-phenylalanine, dl-valine, dl-methionine and $\beta$-alanine, and wherein $p$ has a value of from about 0.06 to about 0.53.

* * * * *